(12) United States Patent
Valgeirsson et al.

(10) Patent No.: US 7,521,480 B2
(45) Date of Patent: Apr. 21, 2009

(54) ARYL UREIDO BENZOIC ACID DERIVATIVES AND THEIR USE

(75) Inventors: Jon Valgeirsson, Reykjavik (IS); Elsebet Østergaard Nielsen, Ballerup (DK); Dan Peters, Ballerup (DK)

(73) Assignee: Neurosearch, Ballerup (DK)

( * ) Notice: Subject to any disclaimer, the term of this patent is extended or adjusted under 35 U.S.C. 154(b) by 437 days.

(21) Appl. No.: 10/535,683

(22) PCT Filed: Nov. 10, 2003

(86) PCT No.: PCT/DK03/00768

§ 371 (c)(1), (2), (4) Date: May 19, 2005

(87) PCT Pub. No.: WO2004/046090

PCT Pub. Date: Jun. 3, 2004

(65) Prior Publication Data

US 2006/0069255 A1   Mar. 30, 2006

(30) Foreign Application Priority Data

Nov. 21, 2002   (DK) ................................ 2002 01803

(51) Int. Cl.
*A61K 31/135* (2006.01)
*C07C 273/00* (2006.01)
*C07C 275/00* (2006.01)

(52) U.S. Cl. ............................ 514/646; 564/32; 564/47

(58) Field of Classification Search ................. 514/646; 564/32, 47
See application file for complete search history.

(56) References Cited

U.S. PATENT DOCUMENTS

| | | | |
|---|---|---|---|
| 2,722,544 A | | 11/1955 | Martin |
| 3,332,981 A | * | 7/1967 | Shultis, Jr. et al. .......... 558/417 |
| 4,405,644 A | | 9/1983 | Kabbe et al. |
| 5,665,675 A | * | 9/1997 | Nagai et al. ................. 503/216 |
| 5,710,094 A | * | 1/1998 | Minami et al. .............. 503/204 |
| 5,811,368 A | * | 9/1998 | Fukuchi et al. ............. 503/209 |
| 5,811,369 A | * | 9/1998 | Nagai et al. ................. 503/209 |
| 6,417,393 B1 | | 7/2002 | Pederson et al. |

FOREIGN PATENT DOCUMENTS

| | | |
|---|---|---|
| EP | 0 656 350 A1 | 6/1995 |
| GB | 709455 A1 | 5/1954 |
| WO | WO-94/22807 A1 | 10/1994 |
| WO | WO-96/25157 A1 | 8/1996 |
| WO | WO-97/29743 A1 | 8/1997 |
| WO | WO-97/45111 A1 | 12/1997 |
| WO | WO-97/45400 A1 | 12/1997 |
| WO | WO-98/47879 A1 | 10/1998 |
| WO | WO-99/00357 A1 | 1/1999 |
| WO | WO-99/38846 A1 | 8/1999 |
| WO | WO-00/24707 A1 | 5/2000 |
| WO | WO-02/39987 A2 | 5/2002 |
| WO | WO-02/064128 A | 8/2002 |
| WO | WO-02/070467 A1 | 9/2002 |
| WO | WO-03/000245 A1 | 1/2003 |
| WO | WO-03/002541 A1 | 1/2003 |
| WO | WO-03/022273 A1 | 3/2003 |

OTHER PUBLICATIONS

Bennekou et al., Database Caplus [Online], Chemical Abstracts Service, Columbus, Ohio, US, retrieved from STN Database Accession No. 2001:169674.
Buckman et al., Database Caplus [Online], Chemical Abstracts Service, Clumbus, Ohio, US, retrieved from STN Accession No. 1998:159564.
Pavia et al, Journal of Medicinal Chemistry, vol. 33, 1990, pp. 854-861.
Valgeirsson et al., Journal of Medicincal Chemistry, vol. 46, No. 26, Dec. 18, 2003, pp. 5834-5843.

* cited by examiner

*Primary Examiner*—Rei-Tsang Shiao
*Assistant Examiner*—Susannah Chung
(74) *Attorney, Agent, or Firm*—Birch, Stewart, Kolasch & Birch, LLP

(57) ABSTRACT

This invention relates to novel aryl ureido benzoic acid derivatives useful as selective and non-competitive antagonists of the ionotropic GluR5 receptor. Due to their biological activity, the aryl ureido derivatives of the invention are considered useful for treating diseases that are responsive to modulation of an aspartate or a glutamate receptor. Moreover the invention provides chemical compounds for use according to the invention, as well as pharmaceutical compositions comprising the chemical compounds, and methods of treating diseases or disorders or conditions responsive to modulation of an aspartate or a glutamate receptor.

3 Claims, No Drawings

ARYL UREIDO BENZOIC ACID DERIVATIVES AND THEIR USE

TECHNICAL FIELD

This invention relates to novel aryl ureido benzoic acid derivatives useful as selective and non-competitive antagonists of the ionotropic GluR5 receptor.

Due to their biological activity, the aryl ureido derivatives of the invention are considered useful for treating diseases that are responsive to modulation of an aspartate or a glutamate receptor.

Moreover the invention provides chemical compounds for use according to the invention, as well as pharmaceutical compositions comprising the chemical compounds, and methods of treating diseases or disorders or conditions responsive to modulation of an aspartate or a glutamate receptor.

BACKGROUND ART

Excitatory neurotransmission in the mammalian central nervous system (CNS) is primarily mediated by the amino acid, L-glutamate, acting on ionotropic and metabotropic receptors. The ionotropic receptors, which respond to this amino acid, have been divided into the N-methyl-D-aspartate (NMDA) receptors, the alfa-amino-3-hydroxy-5-methyl-4-isoxazole propionic acid (AMPA) receptors, and the kainic acid (KA) receptors. Moreover molecular biological studies have established that these receptors are composed of subunits that can assemble to form functional channels, and a number of such subunits have been identified.

This way it has been established that the AMPA receptors are assembled from four protein subunits known as GluR1 to GluR4, while the KA receptors are assembled from subunits known as GluR5 to GluR7, KA-1 and KA-2.

Due to their distribution in different mammalian tissues, the GluR5 receptors and the substances acting thereon have drawn particular attention.

WO 94/22807 describes urea and amide derivatives useful as potassium channel openers.

WO 97/45400, WO 97/45111, WO 98/47879 and WO 00/24707 describe diphenyl urea derivatives containing an acidic group and their use as chloride channel blockers.

WO 02/039987 describes the use of diphenyl urea derivatives as malaria anion channel blockers for treating malaria.

WO 02/064128 describes the use of diphenyl urea derivatives for modulation of the association of caspase-9 to Apaf-1 for the treatment of diseases characterised by excessive or insufficient cell death.

WO 02/070467 describes diphenyl urea derivatives useful as inhibitors of intracellular protein-degradation pathways.

However, use of diphenyl urea derivatives as ionotropic GluR5 receptor modulators have never been described.

SUMMARY OF THE INVENTION

It is an object of the invention to provide novel compounds useful as selective and non-competitive antagonists of the ionotropic GluR5 receptor.

This object is met by the provision of the novel aryl ureido benzoic acid derivatives derivative represented by Formula I,

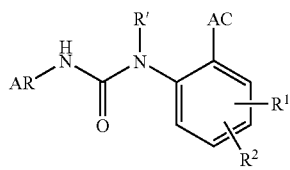

any of its enantiomers or any mixture of its enantiomers, or a pharmaceutically-acceptable addition salt thereof, wherein AC represents an acidic group selected from —$SO_2OH$; —$SO_2NH_2$; a group of the formula —$(CH_2)_n COOH$, wherein n is 0, 1, 2 or 3; a group of the formula —(CX)OH, wherein X represents O or NR", wherein R" represents hydrogen or alkyl; or X together with R' form a heterocyclic ring; and a heterocyclic ring of the structure

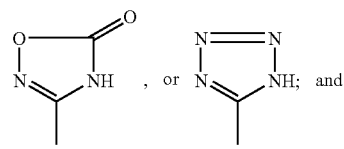

R' represents hydrogen or alkyl; or R' and X together form a heterocyclic ring; and $R^1$ and $R^2$, independently of each another, represents hydrogen, halo, alkyl, cycloalkyl, cycloalkyl-alkyl, haloalkyl, nitro or cyano; and if one of $R^1$ and $R^2$ represents hydrogen, then the other of $R^1$ and $R^2$ is different from hydrogen; and AR represents an aromatic mono-, bi- or polycyclic carbocyclic or heterocyclic group, which aromatic group is optionally substituted one or more times with substituents selected from the group consisting of halo, alkyl, cycloalkyl, cycloalkyl-alkyl, alkenyl, alkynyl, hydroxy, alkoxy, oxo, haloalkyl, nitro, cyano, phenyl or benzyl; or which aromatic group is optionally substituted with a methylenedioxy group or a higher homolog of the structure —O—$(CH_2)_m$—O—, wherein m is 1, 2 or 3.

In another aspect the invention provides pharmaceutical compositions comprising therapeutically effective amounts of a chemical compound of the invention, or a pharmaceutically-acceptable addition salt thereof.

In a further aspect the invention relates to the use of a chemical compound of the invention, or a pharmaceutically-acceptable addition salt thereof, for the manufacture of a pharmaceutical composition/medicament.

In a final aspect, the invention provides a method of treatment, prevention or alleviation of a disease or a disorder or a condition of a living animal body, including a human, which disorder, disease or condition is responsive to modulation of an aspartate or a glutamate receptor, which method comprises the step of administering to said animal body in need thereof a therapeutically effective amount of a chemical compound of the invention, or a pharmaceutically-acceptable addition salt thereof.

Other objects of the invention will be apparent to the person skilled in the art from the following detailed description and examples.

DETAILED DISCLOSURE OF THE INVENTION

In its first aspect the invention provides an aryl ureido derivative represented by Formula I,

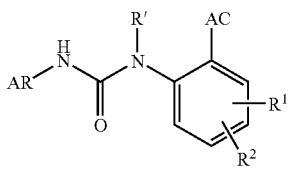

any of its enantiomers or any mixture of its enantiomers, or a pharmaceutically-acceptable addition salt thereof, wherein AC represents an acidic group selected from —SO$_2$OH; —SO$_2$NH$_2$; a group of the formula —(CH$_2$)$_n$COOH, wherein n is 0, 1, 2 or 3; a group of the formula —(CX)OH, wherein X represents O or NR", wherein R" represents hydrogen or alkyl; or X together with R' form a heterocyclic ring; and a heterocyclic ring of the structure

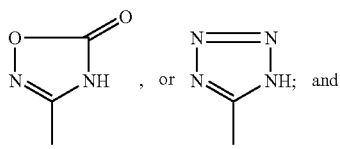

R' represents hydrogen or alkyl; or R' and X together form a heterocyclic ring; and R$^1$ and R$^2$, independently of each another, represents hydrogen, halo, alkyl, cycloalkyl, cycloalkyl-alkyl, haloalkyl, nitro or cyano; and if one of R$^1$ and R$^2$ represents hydrogen, then the other of R$^1$ and R$^2$ is different from hydrogen; and AR represents an aromatic mono-, bi- or polycyclic carbocyclic or heterocyclic group, which aromatic group is optionally substituted one or more times with substituents selected from the group consisting of halo, alkyl, cycloalkyl, cycloalkyl-alkyl, alkenyl, alkynyl, hydroxy, alkoxy, oxo, haloalkyl, nitro, cyano, phenyl or benzyl; or which aromatic group is optionally substituted with a methylenedioxy group or a higher homolog of the structure —O—(CH$_2$)$_m$—O—, wherein m is 1, 2 or 3.

In a preferred embodiment the aryl ureido derivative of the invention is represented by Formula Ia,

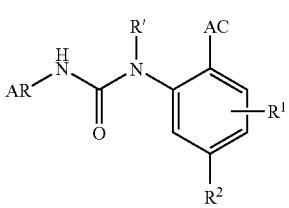

wherein R', R$^1$, R$^2$, AC and AR are as defined above.

In another preferred embodiment the aryl ureido derivative of the invention is represented by Formula I or Ia, wherein AR represents an aromatic mono-, bi- or poly-cyclic carbocyclic group, which aromatic carbocyclic group is optionally substituted one or more times with substituents selected from the group consisting of halo, alkyl, cycloalkyl, cycloalkyl-alkyl, alkenyl, alkynyl, hydroxy, alkoxy, haloalkyl, nitro, cyano, phenyl or benzyl; or which aromatic group is optionally substituted with a methylenedioxy group or a higher homolog of the structure —O—(CH$_2$)$_m$—O—, wherein m is 1, 2 or 3.

In a more preferred embodiment, the aryl ureido derivative of the invention is represented by Formula II,

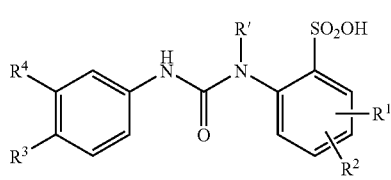

wherein R' represents hydrogen or alkyl;

R$^1$ and R$^2$, independently of each another, represents hydrogen, halo, alkyl, cycloalkyl, haloalkyl, nitro or cyano; and if one of R$^1$ and R$^2$ represents hydrogen, then the other of R$^1$ and R$^2$ is different from hydrogen; and R$^3$ and R$^4$, independently of each another, represent hydrogen, halo, alkyl, cycloalkyl, cycloalkyl-alkyl, alkenyl, alkynyl, hydroxy, alkoxy, oxo, haloalkyl, nitro, cyano, phenyl or benzyl; or R$^3$ and R$^4$ together form a methylenedioxy ring or a higher homolog of the structure —O—(CH$_2$)$_m$—O—, wherein m is 1, 2 or 3; or R$^3$ and R$^4$ together form a benzo-fused ring, which fused ring is optionally substituted one or more times with substituents selected from halo, alkyl, cycloalkyl, cycloalkyl-alkyl, alkenyl, alkynyl, hydroxy, alkoxy, oxo, haloalkyl, nitro, cyano, phenyl or benzyl.

In a more preferred embodiment the aryl ureido derivative of the invention is a compound of Formula II, wherein R' represents hydrogen; and R$^1$ and R$^2$, independently of each another, represents hydrogen, halo, alkyl or cycloalkyl; and if one of R$^1$ and R$^2$ represents hydrogen, then the other of R$^1$ and R$^2$ is different from hydrogen; and R$^3$ and R$^4$, independently of each another, represent hydrogen, halo, hydroxy, alkoxy, oxo, haloalkyl, nitro, cyano or phenyl; or R$^3$ and R$^4$ together form a methylenedioxy ring of the structure —O—CH$_2$—O—; or R$^3$ and R$^4$ together form a benzo-fused ring, which fused ring is optionally substituted one or more times with substituents selected from halo, hydroxy, alkoxy and haloalkyl.

In an even more preferred embodiment the aryl ureido derivative of the invention is a compound of Formula IIa,

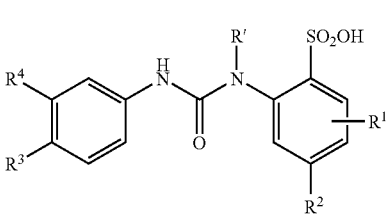

wherein,

R' represents hydrogen or alkyl;

R$^1$ represents hydrogen, halo, alkyl or cycloalkyl;

R$^2$ represents halo, alkyl or cycloalkyl; and

R$^3$ and R$^4$, independently of each another, represent hydrogen, halo, hydroxy, alkoxy, haloalkyl; or R$^3$ and R$^4$ together form a methylenedioxy ring of the structure —O—CH$_2$—O—; or R$^3$ and R$^4$ together form a benzo-fused ring, which fused ring is optionally substituted one or more times with substituents selected from halo, hydroxy, alkoxy and haloalkyl.

In a most preferred embodiment, the aryl ureido derivative of the invention is

2-[3-(3-Bromo-phenyl)-ureido]-4-chloro-5-methyl-benzenesulfonic acid;

4-Chloro-5-methyl-2-[3-(3-trifluoromethyl-phenyl)-ureido]-benzensulphonic acid;

4-Chloro-2-[3-(3-trifluoromethyl-phenyl)-ureido]-benzensulphonic acid;

2-[3-(3-Bromo-phenyl)-ureido]-4-chloro-benzenesulfonic acid; or

4-Chloro-5-methyl-2-(3-naphthalen-2-yl-ureido)-benzensulphonic acid;

or an enantiomer or a mixture of enantiomers, or a pharmaceutically-acceptable addition salt thereof.

In a third preferred embodiment, the aryl ureido derivative of the invention is a compound represented by Formula III

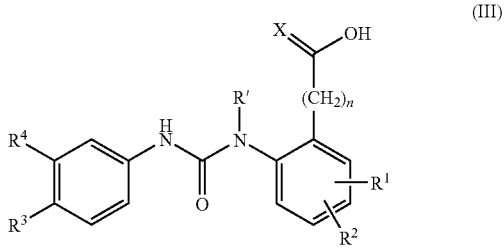

(III)

wherein n is 0, 1 or 2; X represents O or NR", wherein R" represents hydrogen or alky); or R' and X together form a heterocyclic ring, which heterocyclic ring may in particular be a pyrazole, an isoxazole or a pyridazole ring; and R' represents hydrogen or alkyl; or R' and X together form a heterocyclic ring, which heterocyclic ring may in particular be a pyrazole, an isoxazole or a pyridazole ring; and $R^1$ and $R^2$, independently of each another, represents hydrogen, halo, alkyl, cycloalkyl, haloalkyl, nitro or cyano; and if one of $R^1$ and $R^2$ represents hydrogen, then the other of $R^1$ and $R^2$ is different from hydrogen; and $R^3$ and $R^4$, independently of each another, represent hydrogen, halo, alkyl, cycloalkyl, cycloalkyl-alkyl, alkenyl, alkynyl, hydroxy, alkoxy, oxo, haloalkyl, nitro, cyano, phenyl or benzyl; or $R^3$ and $R^4$ together form a methylenedioxy ring or a higher homolog of the structure —O—$(CH_2)_m$—O—, wherein m is 1, 2 or 3; or $R^3$ and $R^4$ together form a benzo-fused ring, which fused ring is optionally substituted one or more times with substituents selected from halo, alkyl, cycloalkyl, cycloalkyl-alkyl, alkenyl, alkynyl, hydroxy, alkoxy, oxo, haloalkyl, nitro, cyano, phenyl or benzyl.

In a fourth preferred embodiment, the aryl ureido derivative of the invention is a compound represented by Formula IV

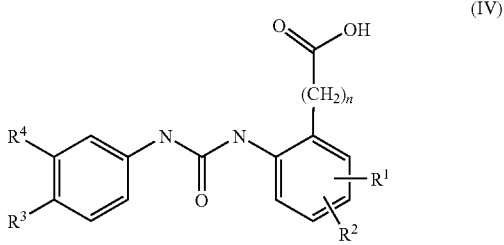

(IV)

wherein n is 0, 1 or 2; and $R^1$ and $R^2$, independently of each another, represents hydrogen, halo, alkyl, cycloalkyl, haloalkyl, nitro or cyano; and if one of $R^1$ and $R^2$ represents hydrogen, then the other of $R^1$ and $R^2$ is different from hydrogen; and $R^3$ and $R^4$, independently of each another, represent hydrogen, halo, alkyl, cycloalkyl, cycloalkyl-alkyl, alkenyl, alkynyl, hydroxy, alkoxy, oxo, haloalkyl, nitro, cyano, phenyl or benzyl; or $R^3$ and $R^4$ together form a methylenedioxy ring or a higher homolog of the structure —O—$(CH_2)_m$—O—, wherein m is 1, 2 or 3; or $R^3$ and $R^4$ together form a benzo-fused ring, which fused ring is optionally substituted one or more times with substituents selected from halo, alkyl, cycloalkyl, cycloalkyl-alkyl, alkenyl, alkynyl, hydroxy, alkoxy, oxo, haloalkyl, nitro, cyano, phenyl or benzyl.

In a more preferred embodiment, the aryl ureido derivative of the invention is a compound of Formula IV, wherein n is 0, 1 or 2; and $R^1$ and $R^2$, independently of each another, represents hydrogen, halo, alkyl or cycloalkyl; and if one of $R^1$ and $R^2$ represents hydrogen, then the other of $R^1$ and $R^2$ is different from hydrogen; and $R^3$ and $R^4$, independently of each another, represent hydrogen, halo, hydroxy, alkoxy, haloalkyl, nitro, cyano or phenyl; or $R^3$ and $R^4$ together form a methylenedioxy ring of the structure —O—$CH_2$—O—; or $R^3$ and $R^4$ together form a benzo-fused ring, which fused ring is optionally substituted one or more times with substituents selected from halo, hydroxy, alkoxy and haloalkyl.

In an even more preferred embodiment, the aryl ureido derivative of the invention is a compound of Formula IVa,

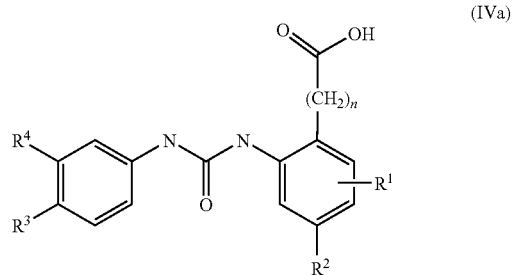

(IVa)

wherein n is 0 or 1;

$R^1$ represents hydrogen, halo, alkyl or cycloalkyl;

$R^2$ represents halo, alkyl or cycloalkyl; and $R^3$ and $R^4$, independently of each another, represent hydrogen, halo, hydroxy, alkoxy, haloalkyl or phenyl; or $R^3$ and $R^4$ together form a methylenedioxy ring of the structure —O—$CH_2$—O—; or $R^3$ and $R^4$ together form a benzo-fused ring, which fused ring is optionally substituted one or more times with substituents selected from halo, hydroxy, alkoxy and haloalkyl.

In a most preferred embodiment, the aryl ureido derivative of the invention is

4-Chloro-2-(3-phenyl-ureido)-benzoic acid;

4-Chloro-2-[3-(2-methoxy-phenyl)-ureido]-benzoic acid;

2-(3-Benzo[1,3]dioxol-5-yl-ureido)-4-chloro-benzoic acid;

4-Chloro-2-[3-(3-trifluoromethyl-phenyl)-ureido]-benzoic acid;

2-(3-Biphenyl-2-yl-ureido)-4-chloro-benzoic acid;

2-(3-Biphenyl-4-yl-ureido)-4-chloro-benzoic acid;

2-[3-(2-Bromo-phenyl)-ureido]-4-chloro-benzoic acid;

4-Chloro-2-[3-(4-fluoro-phenyl)-ureido]-benzoic acid;

4-Chloro-2-[3-(4-iodo-phenyl)-ureido]-benzoic acid;

4-Chloro-2-[3-(4-chloro-phenyl)-ureido]-benzoic acid;

4-Chloro-2-[3-(3-iodo-phenyl)-ureido]-benzoic acid;

4-Chloro-2-[3-(4-methoxy-phenyl)-ureido]-benzoic acid;

4-Chloro-2-[3-(2-trifluoromethyl-phenyl)-ureido]-benzoic acid;

4-Chloro-2-[3-(3-chloro-phenyl)-ureido]-benzoic acid;

4-Chloro-2-(3-naphtalen-2-yl-ureido)-benzoic acid;

4-Chloro-2-[3-(2-iodo-phenyl)-ureido]-benzoic acid;

2-(3-Biphenyl-3-yl-ureido)-4-chloro-benzoic acid;

4-Chloro-2-[3-(4-hydroxy-phenyl)-ureido]-benzoic acid;

4-Chloro-2-[3-(3-hydroxy-phenyl)-ureido]-benzoic acid;

4-Chloro-2-[3-(2-hydroxy-phenyl)-ureido]-benzoic acid; or

{2-[3-(3-Bromo-phenyl)-ureido]-4-chloro-phenyl}-acetic acid;

or an enantiomer or a mixture of enantiomers, or a pharmaceutically-acceptable addition salt thereof.

In a fifth preferred embodiment, the aryl ureido derivative of the invention is a phenyl carbamoyl indazole derivative of Formula V,

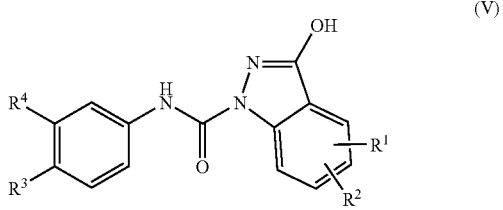

(V)

wherein $R^1$ and $R^2$, independently of each another, represents hydrogen, halo, alkyl, cycloalkyl, haloalkyl, nitro or cyano; and if one of $R^1$ and $R^2$ represents hydrogen, then the other of $R^1$ and $R^2$ is different from hydrogen; and $R^3$ and $R^4$, independently of each another, represent hydrogen, halo, alkyl, cycloalkyl, cycloalkyl-alkyl, alkenyl, alkynyl, hydroxy, alkoxy, oxo, haloalkyl, nitro, cyano, phenyl or benzyl; or $R^3$ and $R^4$ together form a methylenedioxy ring or a higher homolog of the structure —O—(CH$_2$)$_m$—O—, wherein m is 1, 2 or 3; or $R^3$ and $R^4$ together form a benzo-fused ring, which fused ring is optionally substituted one or more times with substituents selected from halo, alkyl, cycloalkyl, cycloalkyl-alkyl, alkenyl, alkynyl, hydroxy, alkoxy, oxo, haloalkyl, nitro, cyano, phenyl or benzyl.

In a more preferred embodiment the aryl ureido benzoic acid derivative of the invention is a compound of Formula V, wherein $R^1$ and $R^2$, independently of each another, represents hydrogen, halo, alkyl or cycloalkyl; and if one of $R^1$ and $R^2$ represents hydrogen, then the other of $R^1$ and $R^2$ is different from hydrogen; and $R^3$ and $R^4$, independently of each another, represent hydrogen, halo, hydroxy, alkoxy, haloalkyl, nitro, cyano or phenyl; or $R^3$ and $R^4$ together form a methylenedioxy ring of the structure —O—CH$_2$—O—; or $R^3$ and $R^4$ together form a benzo-fused ring, which fused ring is optionally substituted one or more times with substituents selected from halo, hydroxy, alkoxy and haloalkyl.

In an even more preferred embodiment the aryl ureido benzoic acid derivative of the invention is a compound of Formula Va,

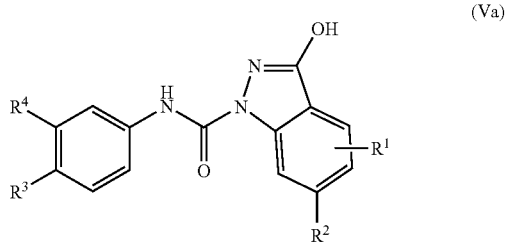

(Va)

wherein $R^1$ represents hydrogen, halo, alkyl or cycloalkyl;

$R^2$ represents halo, alkyl, or cycloalkyl; and $R^3$ and $R^4$, independently of each another, represent hydrogen, halo, hydroxy, alkoxy, haloalkyl, nitro, cyano or phenyl; or $R^3$ and $R^4$ together form a methylenedioxy ring of the structure —O—CH$_2$—O—; or $R^3$ and $R^4$ together form a benzo-fused ring, which fused ring is optionally substituted one or more times with substituents selected from halo, hydroxy, alkoxy and haloalkyl.

In a most preferred embodiment the aryl ureido benzoic acid derivative of the invention is 6-Chloro-3-hydroxy-indazole-1-carboxylic acid naphthalen-2-ylamide;

or an enantiomer or a mixture of enantiomers, or a pharmaceutically-acceptable addition salt thereof.

In a sixth preferred embodiment the aryl ureido benzoic acid derivative of the invention is a compound of Formula I or Ia, wherein AC represents a heterocyclic ring of the structure

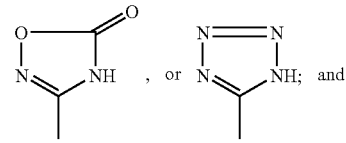

R' represents hydrogen or alkyl; and $R^1$ and $R^2$, independently of each another, represents hydrogen, halo, alkyl, cycloalkyl, haloalkyl, nitro or cyano; and if one of $R^1$ and $R^2$ represents hydrogen, then the other of $R^1$ and $R^2$ is different from hydrogen; and AR represents an aromatic mono-, bi- or polycyclic carbocyclic or heterocyclic group, which aromatic group is optionally substituted one or more times with substituents selected from the group consisting of halo, alkyl, cycloalkyl, cycloalkyl-alkyl, alkenyl, alkynyl, hydroxy, alkoxy, oxo, haloalkyl, nitro, cyano, phenyl or benzyl; or which aromatic group is optionally substituted with a methylenedioxy group or a higher homolog of the structure —O—(CH$_2$)$_m$—O—, wherein m is 1, 2 or 3.

In a seventh preferred embodiment the aryl ureido benzoic acid derivative of the invention is a compound of Formula VI

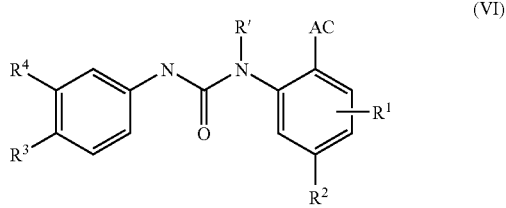

(VI)

wherein
AC represents a heterocyclic ring of the structure

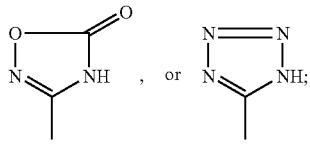

R' represents hydrogen or alkyl;
R$^1$ represents hydrogen, halo, alkyl, cycloalkyl, haloalkyl, nitro or cyano;
R$^2$ represents halo, alkyl, cycloalkyl, haloalkyl, nitro or cyano; and
R$^3$ and R$^4$, independently of each another, represent hydrogen, halo, hydroxy, alkoxy, haloalkyl or phenyl; or R$^3$ and R$^4$ together form a methylenedioxy ring of the structure —O—CH$_2$—O—; or R$^3$ and R$^4$ together form a benzo-fused ring, which fused ring is optionally substituted one or more times with substituents selected from halo, hydroxy, alkoxy and haloalkyl.

In a most preferred embodiment the aryl ureido benzoic acid derivative of the invention is
1-[5-Chloro-2-(5-oxo-4,5-dihydro-[1,2,4]oxadiazol-3-yl)-phenyl]-3-(3-trifluoromethyl-phenyl)-urea;
1-[5-Chloro-2-(5-oxo-4,5-dihydro-[1,2,4]oxadiazol-3-yl)-phenyl]-3-(3-bromo-phenyl)-urea;
1-[5-Chloro-2-(1H-tetrazol-5-yl)-phenyl]-3-naphthalen-2-yl-urea; or
1-[5-Chloro-2-(5-oxo-4,5-dihydro-[1,2,4]oxadiazol-3-yl)-phenyl]-3-naphthalen-2-yl-urea;
or an enantiomer or a mixture of enantiomers, or a pharmaceutically-acceptable addition salt thereof.

In an eight preferred embodiment the aryl ureido benzoic acid derivative of the invention is a compound of Formula VI,

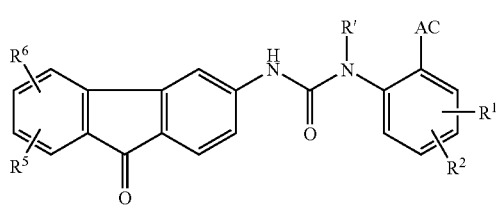

(VII)

wherein AC represents an acidic group selected from
—SO$_2$OH; —SO$_2$NH$_2$; a group of the formula —(CH$_2$)$_n$COOH, wherein n is 0, 1, 2 or 3; a group of the formula —(CX)OH, wherein X represents O or NR'', wherein R'' represents hydrogen or alkyl; or X together with R' form a heterocyclic ring, which heterocyclic ring may in particular be a pyrazole, an isoxazole or a pyridazole ring; and a heterocyclic ring of the structure

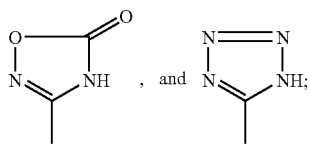

R' represents hydrogen or alkyl; or R' and X together form a heterocyclic ring, which heterocyclic ring may in particular be a pyrazole, an isoxazole or a pyridazole ring;
R$^1$ and R$^2$, independently of each another, represents hydrogen, halo, alkyl, cycloalkyl, haloalkyl, nitro or cyano; and if one of R$^1$ and R$^2$ represents hydrogen, then the other of R$^1$ and R$^2$ is different from hydrogen;
R$^5$ and R$^6$, independently of each another, represent hydrogen, halo, alkyl, cycloalkyl, cycloalkyl-alkyl, alkenyl, alkynyl, hydroxy, alkoxy, oxo, haloalkyl, nitro, cyano, phenyl or benzyl; or R$^5$ and R$^6$ together form a methylenedioxy ring or a higher homolog of the structure —O—(CH$_2$)$_m$—O—, wherein m is 1, 2 or 3.

In a more preferred embodiment the aryl ureido benzoic acid derivative of the invention is a compound of Formula VI, wherein AC represents —(CH$_2$)$_n$COOH, wherein n is 0, 1 or 2; and R' represents hydrogen; and R$^1$ and R$^2$, independently of each another, represents hydrogen, halo, alkyl, cycloalkyl, haloalkyl, nitro or cyano; and if one of R$^1$ and R$^2$ represents hydrogen, then the other of R$^1$ and R$^2$ is different from hydrogen.

In an even more preferred embodiment the aryl ureido benzoic acid derivative of the invention is a compound of Formula VIIa,

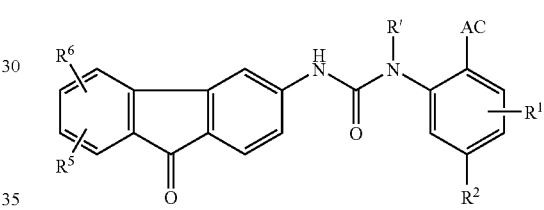

(VIIa)

wherein
AC represents —(CH$_2$)$_n$COOH, wherein n is 0, 1 or 2;
R' represents hydrogen or alkyl;
R$^1$ represents hydrogen, halo, alkyl, cycloalkyl, haloalkyl, nitro or cyano;
R$^2$ represents halo, alkyl, cycloalkyl, haloalkyl, nitro or cyano; and
R$^5$ and R$^6$, independently of each another, represent hydrogen, halo, alkyl, cycloalkyl, hydroxy, alkoxy and/or haloalkyl.

In a most preferred embodiment the aryl ureido benzoic acid derivative of the invention is
4-Chloro-2-[3-(9-oxo-9H-fluoren-3-yl)-ureido]-benzoic acid;
or an enantiomer or a mixture of enantiomers, or a pharmaceutically-acceptable addition salt thereof.

In a ninth preferred embodiment AR represents an aromatic mono-, bi- or poly-cyclic heterocyclic group, which aromatic heterocyclic group is optionally substituted one or more times with substituents selected from the group consisting of halo, alkyl, cycloalkyl, cycloalkyl-alkyl, alkenyl, alkynyl, hydroxy, alkoxy, oxo, haloalkyl, nitro, cyano, phenyl or benzyl; or which aromatic group is optionally substituted with a methylenedioxy group or a higher homolog of the structure —O—(CH$_2$)$_m$—O—, wherein m is 1, 2 or 3; and AC, R', R$^1$ and R$^2$ are as defined above.

In a more preferred embodiment AR represents an aromatic 5-membered monocyclic heterocyclic group selected from furanyl, thienyl and pyrrolyl; or an aromatic 6-membered monocyclic heterocyclic group selected from pyridyl, pyridazinyl, pyrimidinyl and pyrazinyl; or an aromatic bicyclic heterocyclic group selected from indolyl, isoindolyl, benzo[b]furanyl, benzo[b]thienyl, benzimidazolyl and benzothiazolyl; which aromatic heterocyclic group is optionally substituted one or more times with substituents selected from the group consisting of halo, alkyl, cycloalkyl, cycloalkylalkyl, alkenyl, alkynyl, hydroxy, alkoxy, oxo, haloalkyl, nitro, cyano, phenyl or benzyl; and AC, R', $R^1$ and $R^2$ are as defined above.

In an even more preferred embodiment AC represents —$SO_2OH$; —$SO_2NH_2$; or a group of the formula —$(CH_2)_n$COOH, wherein n is 0, 1 or 2; and R' represents hydrogen or alkyl; or R' and X together form a heterocyclic ring, which heterocyclic ring may in particular be a pyrazole, an isoxazole or a pyridazole ring; and $R^1$ and $R^2$, independently of each another, represents hydrogen, halo, alkyl, cycloalkyl, haloalkyl, nitro or cyano; and if one of $R^1$ and $R^2$ represents hydrogen, then the other of $R^1$ and $R^2$ is different from hydrogen.

In a further preferred embodiment and the aryl ureido benzoic acid derivative of the invention is a compound of Formula VIII

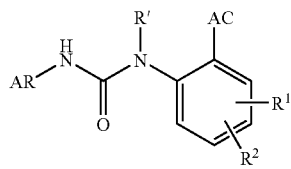

(VIII)

wherein
AC represents —$SO_2OH$, —$SO_2NH_2$, or —COOH;
R' represents hydrogen or alkyl;
$R^1$ represents hydrogen, halo, alkyl, cycloalkyl, haloalkyl, nitro or cyano;
$R^2$ represents halo, alkyl, cycloalkyl, haloalkyl, nitro or cyano; and
AR represents thienyl, pyridyl or indolyl.

In a still further preferred embodiment and the aryl ureido benzoic acid derivative of the invention is a compound of Formula VIIIa

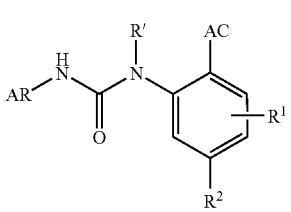

(VIIIa)

wherein
AC represents —$SO_2OH$, —$SO_2NH_2$, or —COOH;
R' represents hydrogen or alkyl;
$R^1$ represents hydrogen, halo, alkyl, cycloalkyl, haloalkyl;
$R^2$ represents halo, alkyl, cycloalkyl or haloalkyl; and
AR represents 2- or 3-thienyl, 2-, 3- or 4-pyridyl or 2- or 3-indolyl.

In a most preferred embodiment the aryl ureido benzoic acid derivative of the invention is
4-Chloro-2-[3-(2-iodo-phenyl)-ureido]-benzoic acid;
4-Chloro-2-(3-thiophen-2-yl-ureido)-benzoic acid;
4-Chloro-2-(3-pyridin-2-yl-ureido)-benzoic acid;
4-Chloro-2-[3-(1H-indol-2-yl)-ureido]-5-methyl-benzenesulfonic acid; or
4-Chloro-2-[3-(1H-indol-2-yl)-ureido]-benzensulphonic acid;

or an enantiomer or a mixture of enantiomers, or a pharmaceutically-acceptable addition salt thereof.

Any combination of two or more of the embodiments described herein is considered within the scope of the present invention.

Definition of Substituents

In the context of this invention halo represents a fluorine, a chlorine, a bromine or an iodine atom.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a haloalkyl group designates an alkyl group as defined herein, which alkyl group is substituted one or more times with halo, as defined above. Preferred haloalkyl groups of the invention include trihalomethyl, in particular trifluoromethyl, and trihalomethyl, in particular 2,2,2-trifluoroethyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl (allyl); 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octtrienyl, or 1,3,5,7-octtetraenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of rom two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention an aromatic mono-, bi- or poly-cyclic carbocyclic group is a mono-, bi- or poly-cyclic carbocyclic group holding carbon only as ring atom. Preferred aromatic carbocyclic groups of the invention include phenyl, indenyl, naphthyl, azulenyl, fluorenyl, and anthracenyl.

In the context of this invention an aromatic mono-, bi- or poly-cyclic heterocyclic group is a mono-, bi- or polycyclic compound, which holds one or more heteroatoms in its ring structure. The term "bi- and poly-heterocyclic groups" includes benzo-fused five- and six-membered heterocyclic rings containing one or more heteroatoms. Preferred heteroatoms include nitrogen (N), oxygen (O), and sulphur (S).

Preferred aromatic monocyclic heterocyclic groups of the invention include 5- and 6 membered heterocyclic groups, including furanyl, in particular 2- or 3-furanyl; thienyl, in particular 2 or 3-thienyl; selenophenyl, in particular 2- or 3-selenophenyl; pyrrolyl (azolyl), in particular 2 or 3-pyrrolyl; oxazolyl, in particular oxazol-2,4 or 5-yl; thiazolyl, in particular thiazol-2,4 or 5-yl; imidazolyl, in particular 2 or 4-imidazolyl; pyrazolyl, in particular 3 or 4-pyrazolyl; isoxazolyl, in particular isoxazol-3,4 or 5-yl; isothiazolyl, in particular isothiazol-3,4 or 5-yl; oxadiazolyl, in particular 1,2,3-oxadiazol-4 or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4 or 5-yl, or 1,3,4-thiadiazol-2-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; and triazinyl, in particular 1,2,4- or 1,3,5-triazinyl.

Preferred aromatic bicyclic heterocyclic groups of the invention include indolizinyl, in particular 2,5 or 6-indolizinyl; indolyl, in particular 2,5 or 6-indolyl; isoindolyl, in particular 2,5 or 6-isoindolyl; benzo[b]furanyl, in particular 2, 5 or 6-benzofuranyl; benzo[b]thienyl, in particular 2,5 or 6-benzothienyl; benzoimidazolyl, in particular 2,5 or 6-benzoimidazolyl; benzothiazolyl, in particular 5 or 6-benzothiazolyl; purinyl, in particular 2 or 8-purinyl; quinolinyl, in particular 2,3,6 or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; and pteridinyl, in particular 2,6 or 7-pteridinyl.

Pharmaceutically Acceptable Salts

The aryl ureido derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of the aryl ureido derivatives of the invention include alkali metal salts such as the sodium salt of a chemical compound of the invention containing a carboxy group.

Steric Isomers

The aryl ureido derivatives of the invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the invention can thus be resolved into their optical antipodes, e.g., by fractional crystallisation of d- or l-(tartrates, mandelates, or camphor-sulphonate) salts for example.

The aryl ureido derivatives of the invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The aryl ureido derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The aryl ureido derivatives of the present invention were found to be modulators of the ionotropic glutamate receptors, and in particular of the ionotropic GluR5 receptor. In a preferred embodiment the invention the aryl ureido derivatives are useful as selective, non-competitive antagonists of the ionotropic GluR5 receptor.

It is currently believed that compounds that modify neurotransmission by interaction with the aspartate and glutamate receptors are useful in the treatment of a variety of disorders of the CNS and PNS and disorders of other origin, including chronic or acute pain, neuropathic pain, intractable pain, migraine headaches, neurological and psychiatric disorders, depression, anxiety, psychosis, schizophrenia, excitatory amino acid-dependent psychosis, cognitive disorders, dementia, senile dementia, AIDS-induced dementia, stress-related psychiatric disorders, stroke, global and focal ischaemic or haemorrhagic stroke, cerebral hypoxia/ischaemia, cerebral infarction or cerebral ischaemia resulting from thromboembolic or haemorrhagic stroke, cardiac infarction, brain trauma, brain oedema, cranial/brain trauma, spinal cord trauma, bone-marrow lesions, hypoglycaemia, anoxia, neuronal damage following hypoglycaemia, hypotonia, hypoxia, perinatal hypoxia, cardiac arrest, acute and chronic neurodegenerative diseases or disorders and brain ischaemia of various origin, CNS degenerative disorders, Parkinson's disease, Alzheimer's disease, Huntington's disease, idiopathic and drug induced Parkinson's Disease, amyotrophic lateral sclerosis (ALS), post-acute phase cerebral lesions or chronic diseases of the nervous system, cerebral deficits subsequent to cardiac bypass surgery and grafting, perinatal asphyxia, anoxia from drowning, pulmonary surgery and cerebral trauma, hypoxia-induced nerve cell damage (e.g. in cardiac arrest or bypass operation, or neonatal distress), epilepsy, status epilepticus, seizure disorders, cerebral vasospasm, CNS-mediated spasms, motility disorders, muscular spasms, urinary incontinence, convulsions, disorders responsive to anticonvulsants, autoimmune diseases, emesis, nausea, obesity, chemical dependencies and addictions, addictions and withdrawal symptoms, drug or alcohol induced deficits, drug addiction, ocular damage, retinopathy, retinal neuropathy, tinnitus, tardive dyskinesia.

In a more preferred embodiment the aryl ureido derivatives of the invention are used for the treatment of cognitive and neurodegenerative disorders, movement disorders, depression, AD, ADHD, psychosis and associated cognitive deficits, drug-induced psychosis, drug withdrawal symptoms, stroke, pain, in particular chronic or acute pain, neuropathic pain, intractable pain, or migraine and migraine headaches, epilepsy and retinopathy.

In a particularly preferred embodiment the aryl ureido derivatives of the invention are used for the treatment of pain, in particular chronic or acute pain, neuropathic pain and intractable pain, migraine, migraine headaches.

In another particularly preferred embodiment the aryl ureido derivatives of the invention are used for the treatment of epilepsy, status epilepticus or a seizure disorder.

Pharmaceutical Compositions

In another aspect the invention provides novel pharmaceutical compositions comprising a therapeutically effective amount of the aryl ureido derivative the invention.

While the aryl ureido derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the aryl ureido derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the diagnosis, treatment, prevention or alleviation of a disease or a disorder or a condition of a living animal body, including a human, which disorder, disease or condition is responsive to modulation of an aspartate or a glutamate receptor, comprising the step of administering to such a living animal body, including a human, in need thereof a therapeutically effective amount of a chemical compound of the invention, or a pharmaceutically-acceptable addition salt thereof.

The preferred indications contemplated according to the invention are those stated above.

In a preferred embodiment, the disorder, disease or condition is chronic or acute pain, neuropathic pain, intractable pain, migraine or migraine headaches.

In a more preferred embodiment, the disorder, disease or condition is epilepsy, status epilepticus or a seizure disorder.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

Starting Materials

2-Amino-4-chloro-benzenesulfonic acid

Concentrated sulphuric acid (specific gravity. 1.84) (13.9 ml, 250 mmol) was diluted with 100 ml of water. 3-Chloroaniline (31.9 g, 250 mmol) was added over 30 minutes while temperature was kept at 85° C. During the addition some precipitation occurred. The suspension was allowed to cool to room temperature and heavy precipitation was formed. The solid is filtered with suction to yield white crystalline solid. The solid was heated slowly to 200° C. under vacuum (water pump) and fitted with a water trap. The solid was kept at 200° C. for 7 hours. Water was lost from the crystalline material. The solid was allowed to cool and then dissolved in dilute aqueous NaOH and precipitated with hydrochloric acid. Yielded 25 g (48%) of the title compound as a white crystalline solid (m.p. >250° C.).

2-Amino-4-chloro-N-hydroxy-benzamide

2-Amino-4-chloro-benzonitrile (5.3 g, 35 mmol) was dissolved in ethanol (180 ml) aided by heating. An aqueous solution of hydroxylamine hydrochloride (4.9 g, 70 mmol) and sodium bicarbonate (11.1 g, 105 mmol) was added and the mixture was refluxed for 8 hours. The solvent was then reduced and the product suspended in water (100 ml) and filtered off to yield 5.6 g (86%) of a white powder (m.p. 131-133° C.).

3-(2-Amino-4-chloro-phenyl)-4H-[1,2,4]oxadiazol-5-one

Sodium metal (0.92 g, 40 mmol) was dissolved in 70 ml absolute ethanol and 2-amino-4-chloro-N-hydroxy-benzamide (3.71 g, 20 mmol) was added and then diethyl carbonate (9.44 g, 80 mmol) was added. The mixture was refluxed for 18 hours and then reduced to dryness under vacuum and triturated with 0.5 M aqueous HCl, filtered and then triturated with toluene and filtered to yield 3.4 g (80%) of red-brown solid (m.p. 159-161° C.).

Individual Methods

2-[3-(3-Bromo-phenyl)-ureido]-4-chloro-5-methyl-benzenesulfonic acid (Compound 1a)

2-Amino-4-chloro-5-methyl-benzenesulfonic acid (665 mg, 3.0 mmol) was suspended in 30 ml dry THF and 1-bromo-3-isocyanato-benzene (624 mg, 3.15 mmol) was added. Upon addition of triethylamine (354 mg, 3.15 mmol) the suspension cleared and became a solution. The solution was stirred at room temperature overnight. The reaction mixture was diluted with ethyl acetate (150 ml) and washed with diluted aqueous hydrochloric acid. The organic phase was dried over sodium sulphate and reduced to dryness under vacuum. The title compound was recrystallised from ethyl acetate/heptane to give 820 mg (65%) of white crystals (m.p. 275° C.; decomposition).

6-Chloro-3-hydroxy-indazole-1-carboxylic acid naphthalen-2-ylamide (Compound 1b)

2-Amino-4-chloro-benzoic acid (17.16 g, 100 mmol) was suspended in 90 ml of water and 20 ml of concentrated HCl. NaNO$_2$ (6.9 g, 100 mmol) was dissolved in 15 ml water and added slowly at 0° C. The mixture was stirred at 0° C. for 30 minutes and Na$_2$SO$_3$ (34.0 g, 270 mmol) were added, dissolved in 150 ml water. The mixture was then stirred for 2 hours at room temperature. 30 ml of concentrated HCl were added and the mixture stirred overnight at room temperature and then at 80° C. for 2 hours. The solution is treated with aqueous NaOH until the pH is 5.5 and the precipitated was filtered and triturated with ethanol to yield 13.8 g (82%) of 6-chloro-1H-indazol-3-ol. 6-Chloro-1H-indazol-3-ol (700 mg, 4.15 mmol) was dissolved in 25 ml pyridine together with 1-bromo-3-isocyanato-benzene (990 mg, 5 mmol) and stirred at RT for 4 hours. The mixture was then diluted with EtOAc (100 ml) and washed 2× with 1 M HCl. The organic phase was dried with Na$_2$SO$_4$ and reduced under vacuum. The residue was now dissolved in 1 M NaOH and washed with EtOAc and then precipitated with HCl and the precipitate extracted into EtOAc, dried and reduced under vacuum. The product was then recrystallised from EtOAc and heptane to yield 1.1 g (79%) of crystalline solid (m.p. 223-225° C.).

{2-[3-(3-Bromo-phenyl)-ureido]-4-chloro-phenyl}-acetic acid (Compound 1c)

6-Chlorooxindole (2.5 g, 14.9 mmol) was suspended in 50 ml 4 M aqueous NaOH and the mixture was refluxed for 6 hours. The reaction mixture was allowed to cool and the product precipitated and filtered off with suction. The solid was dissolved in water (100 ml) and precipitated with 4 M aqueous HCl at 0° C. The solid was then filtered with suction and dried under vacuum to yield 2.0 g (72%) of white crystalline solid. (2-Amino-4-chloro-phenyl)-acetic acid (700 mg, 3.8 mmol) was then dissolved in 25 ml pyridine and 1-bromo-3-isocyanato-benzene (811 mg, 4.1 mmol) was added drop-wise and the solution was stirred for 90 minutes. The reaction mixture was diluted with 150 ml ethyl acetate and washed twice with 1 M aqueous HCl. The organic phase was reduced under vacuum and the product recrystallised from ethyl acetate/heptane to yield 680 mg of white crystalline solid (47%) (m.p. 195-196° C.)

Method A

2-[3-(3-Bromo-phenyl)-ureido]-4-chloro-benzenesulfonic acid, triethylammonium salt (Compound A1)

2-Amino-4-chloro-5-benzenesulfonic acid (623 mg, 3 mmol) was suspended in 40 ml dry THF and 1-bromo-3-isocyanato-benzene (693 mg, 3.5 mmol) was added. Upon addition of triethylamine (354 mg, 3.5 mmol) the suspension cleared and became a solution. The solution was stirred at room temperature for 1 hour. The reaction mixture was reduced to dryness under vacuum. The title compound was recrystallised from ethyl acetate/heptane to give 1060 mg (70%) of white crystals (m.p. 178-179° C.) of the title compound.

4-Chloro-5-methyl-2-[3-(3-trifluoromethyl-phenyl)-ureido]-benzensulphonic acid, triethylammonium salt (Compound A2)

Was made according to method A (m.p. 182-183° C.).

4-Chloro-2-[3-(3-trifluoromethyl-phenyl)-ureido]-benzensulphonic acid, triethylammonium salt (Compound A3)

Was made according to method A (m.p. 174-176° C.).

Method B

4-Chloro-2-[3-(1H-indol-2-yl)-ureido]-5-methyl-benzenesulfonic acid (Compound B1)

Indole-2-carboxylic acid (1.29 g, 8.0 mmol) was suspended in 20 ml dry toluene and diphenyl-phosphoryl azide (2.64 g, 9.6 mmol) added. Triethylamine (0.816 g, 8.0 mmol) was then added drop-wise and the mixture stirred at room temperature for 0.5 hour. The solution was heated to 80° C. and the suspension cleared immediately. Then 2-Amino-4-chloro-5-methyl-benzenesulfonic acid (1.661 g, 8.0 mmol) was added and triethylamine (0.816 g, 8.0 mmol). The mixture was stirred for 3 hours at 80° C. and then the reaction mixture was diluted with 200 ml ethyl acetate and washed with saturated aqueous sodium bicarbonate. The organic phase was then extracted 3 times with distilled water. The title compound was precipitated from the aqueous phase with addition of HCl, filtered and recrystallised from ethyl acetate/heptane to yield 1.6 g (53%) of title compound as light purple crystalline solid (m.p. 284-286° C.; decomposition).

4-Chloro-2-[3-(1H-indol-2-yl)-ureido]-benzensulphonic acid (Compound B2)

Was made according to method B (m.p. 277-279° C.; decomposition).

Method C

4-Chloro-2-(3-phenyl-ureido)-benzoic acid (Compound C1)

2-Amino-4-chloro-benzoic acid (515 mg, 3.0 mmol) was suspended in dry THF (5 ml) and phenylisocyanate (429 mg, 3.6 mmol) was added. Triethylamine (303 mg, 3.0 mmol) was added and the mixture was stirred for 2 hours. The mixture was diluted with 75 ml ethyl acetate and extracted into 150 ml 1 M aqueous NaOH, and washed once with 50 ml ethyl acetate. The aqueous phase was then acidified with 4 M aqueous HCl and the product extracted with 2×100 ml ethyl acetate. The organic solvent was dried (Na$_2$SO$_4$) and reduced under vacuum, and the product recrystallised from acetone/water to yield 680 mg (78%) of off-white crystals (m.p. 186-188° C.).

4-Chloro-2-[3-(2-methoxy-phenyl)-ureido]-benzoic acid (Compound C2)

Was made using method C (m.p. 181-183° C.).

2-(3-Benzo[1,3]dioxol-5-yl-ureido)-4-chloro-benzoic acid (Compound C3)

Was prepared using method C (m.p. 183-185° C.)

4-Chloro-2-[3-(3-trifluoromethyl-phenyl)-ureido]-benzoic acid (Compound C4)

Was prepared using method C (m.p. 179-182° C.)

2-(3-Biphenyl-2-yl-ureido)-4-chloro-benzoic acid (Compound C5)

Was prepared using method C (m.p. 208-209° C.).

2-(3-Biphenyl-4-yl-ureido)-4-chloro-benzoic acid (Compound C6)

Was prepared using method C (m.p. 193-194° C.).

2-[3-(2-Bromo-phenyl)-ureido]-4-chloro-benzoic acid (Compound C7)

Was prepared using method C (m.p. 195-197° C.).

4-Chloro-2-[3-(4-fluoro-phenyl)-ureido]-benzoic acid (Compound C8)

Was prepared using method C (m.p. 194-195° C.).

4-Chloro-2-[3-(4-iodo-phenyl)-ureido]-benzoic acid (Compound C9)

Was prepared using method C (m.p. 209-210; decomposition).

4-Chloro-2-[3-(4-chloro-phenyl)-ureido]-benzoic acid (Compound C10)

Was prepared using method C (m.p. 205-207° C.).

4-Chloro-2-[3-(3-iodo-phenyl)-ureido]-benzoic acid (Compound C11)

Was prepared using method C (m.p. 192-193° C.).

4-Chloro-2-[3-(4-methoxy-phenyl)-ureido]-benzoic acid (Compound C12)

Was prepared using method C (m.p. 194-195° C.).

4-Chloro-2-[3-(2-trifluoromethyl-phenyl)-ureido]-benzoic acid (Compound C13)

Was prepared using method C (m.p. 173-175° C.).

4-Chloro-2-[3-(3-chloro-phenyl)-ureido]-benzoic acid (Compound C14)

Was prepared using method C (m.p. 207-209° C.).

Method D

1-[5-Chloro-2-(5-oxo-4,5-dihydro-[1,2,4]oxadiazol-3-yl)-phenyl]-3-(3-trifluoromethyl-phenyl)-urea (Compound D1)

3-(2-Amino-4-chloro-phenyl)-4H-[1,2,4]oxadiazol-5-one (400 mg, 1.92 mmol) was dissolved in 20 ml dry THF and 3-trifluoromethyl-phenyl-isocyanate (450 mg, 2.40 mmol) was added and the reaction stirred for 16 hours. The solvent was reduced under vacuum and the product recrystallised from ethyl acetate and heptane to yield 480 mg (63%) of off-white crystalline solid (m.p. 246-248; decomposition).

1-[5-Chloro-2-(5-oxo-4,5-dihydro-[1,2,4]oxadiazol-3-yl)-phenyl]-3-(3-bromo-phenyl)-urea (Compound D2)

Was made using method D (m.p. 210-211° C.; decomposes).

Method E

4-Chloro-2-(3-pyridin-2-yl-ureido)-benzoic acid (Compound E1)

Pyridine-2-carboxylic acid (369 mg, 3 mmol) was suspended in 15 ml dry toluene and diphenyl-phosphoryl azide (958 mg, 3.5 mmol) added. Triethylamine (354 mg, 3.6 mmol) was then added drop-wise and the mixture stirred at room temperature for 0.5 hour. The solution was heated to 80° C. and after 2 hours 2-amino-4-chloro-benzoic acid (463 mg, 2.7 mmol) was added in 20 ml THF and triethylamine (0.354 g, 3.6 mmol) was also added. The mixture was stirred for 1 hour at 80° C. and then at room temperature overnight. The mixture was allowed to cool and the solvent was removed under reduced pressure. The residue was taken up into ethyl acetate and precipitated with heptane and filtered with suction. Yield after recrystallation from ethyl acetate/heptane was 640 mg (73%) of white crystalline solid (m.p. 222-224° C.).

4-Chloro-2-(3-naphtalen-2-yl-ureido)-benzoic acid (Compound E2)

Was made using method E (m.p. 176-179° C.).

4-Chloro-2-[3-(9-oxo-9H-fluoren-3-yl)-ureido]-benzoic acid (Compound E3)

Was made using method E (m.p. 260-263° C.; decomposition).

4-Chloro-2-[3-(2-iodo-phenyl)-ureido]-benzoic acid (Compound E4)

Was made using method E (m.p 198-201° C.).

4-Chloro-2-[3-(2-iodo-phenyl)-ureido]-benzoic acid (Compound E5)

Was made using method E (M.p >300° C.).

4-Chloro-5-methyl-2-(3-naphthalen-2-yl-ureido)-benzensulphonic acid (Compound E6)

Was prepared using method E (m.p. >300° C.).

1-[5-Chloro-2-(1H-tetrazol-5-yl)-phenyl]-3-naphthalen-2-yl-urea (Compound E7)

Was prepared using method E (m.p. 167-169° C.; decomposition).

1-[5-Chloro-2-(5-oxo-4,5-dihydro-[1,2,4]oxadiazol-3-yl)-phenyl]-3-naphthalen-2-yl-urea (Compound E8)

Was prepared using method E (m.p. 245° C.; decomposition).

2-(3-Biphenyl-3-yl-ureido)-4-chloro-benzoic acid (Compound E9)

p-Iodo-benzoic acid (4.96 g, 20 mmol), phenyl boronic acid (2.68 g, 22 mmol), $Na_2CO_3$ (6.36 g, 60 mmol) and $Pd(OAc)_2$ (44 mg) were dissolved in 80 ml water and heated to 50° C. for 1 hour. Filtered and washed EtOAc, then acidified with 1 M HCl and extracted into EtOAc, dried with $Na_2SO_4$, evaporated and recrystallised from EtOAc and heptane to yield 3.9 g of meta-phenyl benzoic acid as a white solid. 2-(3-Biphenyl-3-yl-ureido)-4-chloro-benzoic acid was then prepared according to method E (m.p. 181-183° C.).

4-Chloro-2-(3-thiophen-2-yl-ureido)-benzoic acid (Compound E10)

Was prepared using method E (m.p. 199-200° C.)

Method F

4-Chloro-2-[3-(4-hydroxy-phenyl)-ureido]-benzoic acid (Compound F1)

4-Chloro-2-[3-(2-methoxy-phenyl)-ureido]-benzoic acid (430 mg, 1.5 mmol) was suspended in 100 ml $CH_2Cl_2$ at 0° C., and $BBr_3$ (1.8 ml, 1.0 M in hexane, 1.8 mmol) was added. The mixture was stirred overnight and more $BBr_3$ (0.9 ml, 1.0 M in hexane, 0.9 mmol) was added followed by additional stirring overnight. The mixture was wash with water and reduced under vacuum. The title compounds was recrystallised from acetone/water to yield 310 mg (73%) white solid (m.p. 212-214° C.; decomposition).

4-Chloro-2-[3-(3-hydroxy-phenyl)-ureido]-benzoic acid (Compound F2)

Was prepared using method F (m.p. 209-211° C.).

4-Chloro-2-[3-(2-hydroxy-Phenyl)-ureido]-benzoic acid (Compound F3)

Was prepared using method F (m.p. 179-180° C.; decomposition).

Example 2

GluR5 and GluR6 Functional Assay

This example describes cell-based assays carried out using human embryonic HEK 293 cells stably expressing GluR5 and GluR6 receptors, respectively, in which assays the inhibition of domoate-induced increase in $Ca_i$ is used as a measure for glutamate antagonist activity of test substances.

The intracellular free calcium concentration ($Ca_i$) is regulating the majority of metabolic processes in mammalian cells. Elevations of $Ca_i$ in excitable tissues such as neurones are seen after specific activation of receptor operated calcium channels (e.g. glutamate, receptors), or after depolarisation and opening of voltage operated calcium channels. Some neurotransmitters and neuro-modulator increase $Ca_i$ by activating G-protein coupled ionophors or by release of $Ca_i$ from intracellular stores via the second messenger $IP_3$.

$Ca_i$ is determined by fluorometric methods in a Fluorescent Image Plate Reader (FLIPR). Calcium-chelating fluorochromes (tetracarboxylic acids) are loaded into the cells as acetoxymethyl esters and subsequently released by an unspecific intracellular esterase. The free acids, which are impermeable to the cell membrane, are maintained in the cell for hours. The fluorescence spectrum (either $EX_{max}$, $EM_{max}$ or both) is changed by the binding of calcium, and the fluorescence is directly proportional to the $Ca_i$.

The present method uses the fluorochromes Fluo-3 or Fluo-4 as the calcium-chelator. Fluo-3/Fluo-4 is virtually non-fluorescent without calcium, but the calcium-Fluo-3/Fluo-4 complexes show a bright fluorescence ($EM_{max}$=526 nm) after excitation around 500 nm ($EX_{max}$=505 nm). This fluorescence spectrum is similar to the spectrum of fluorescein. Since excitation and emission is in the visible light region of the spectrum, standard equipment without quarts optics may be used.

The kainate subtype of ionotropic glutamate receptors exists of two high affinity subunits—KA1 and KA2, and three low affinity subunits—GluR5-7. The ion channel in the GluR5 receptor subtype can be made permeable for calcium by substitution of an arginine (R) to a glutamine (Q) in the pore region. The stably expressed human GluR5 receptors used here are calcium permeable (Q), which makes them ideal for fluorescence measurements.

Cell Culture

GluR5 expressing, respectively GluR6 expressing HEK 293 cells are grown in DMEM containing 10% foetal calf serum, in polystyrene culture flasks (175 cm²) in a humidified atmosphere of 5% $CO_2$ in air, at 37° C. Confluence of cells should be 80-90% on day of plating. GluR5 cells are rinsed with 10 ml of PBS, then added 1.5 ml of Trypsin-EDTA and left in the incubator for 5 min. After addition of 10 ml of growth media cells are re-suspended by trituration with a 10 ml pipette 15 times.

The cells are seeded at a density of $0.5-1\times10^6$ cells/ml (100 μl/well) in black-walled, clear bottom, 96-well plates pretreated with 0.001% PEI solution (75 μl/well for ≧30 min). Plated cells were allowed to proliferate for 24 h before loading with dye.

Loading with Fluo-4-AM

Fluo-4-AM (1 mg, Molecular Probes) is added 912 μl DMSO containing 25 mg/150 μl Pluoronic F-127 (Molecular Probes). The Fluo-4-AM stock solution (1 mM) is diluted with DMEM to a final concentration of 2 μM Fluo-4-AM.

The media is removed from the wells, and 50 μl of the Fluo-4-AM loading solution is added to each well. The plate is sealed and incubated at room temperature for 60 min.

Calcium Measurements

After the loading period, the loading media is aspirated and the cells are washed twice with 100 μl $Na^+$ free Ringer (NN: 10 mM HEPES, 140 mM Choline chloride, 5 mM KCl, 1 mM $MgCl_2$, 10 mM $CaCl_2$, pH 7.4) to remove extracellular dye. 100 μl NN is added to each well, and the fluorescence is measured in the FLIPR.

Cells are pre-incubated for 1.5 min with test compound (50 μl) before addition of domoate (50 μl) to a final concentration of 2 μM when determined on GluR5 and 0.2 μM when determined on GluR6.

Stock solutions of test substances are made in 48% ethanol, 50% DMSO or 100% DMSO. The final concentration of ethanol or DMSO in the well must not exceed 0.1%. Dilutions are done in NN in clear V-bottom plates.

FLIPR Settings
Temperature: 25° C.
Preincubation: 50 μl test solution at a rate of 30 μl/sec and starting height of 100 μl
Antagonist phase: 50 μl domoate solution (8 μM) at a rate of 35 μl/sec and starting height of 150 μl
Reading intervals: preincubation—10 sec×7 and 3 sec×3 antagonist phase—3 sec×17 and 10 sec×12

Addition plates (diluted compound plate and domoate plate) are placed on the far right and left positions in the FLIPR tray. Cell plates are placed in the middle position. Run the preincubation phase test first by using the above settings. The FLIPR will pick up the desired amount from the compound plate and pipette into the cell plate. FLIPR will then take the appropriate measurements in accordance with the interval settings above.

Results

Fluorescence at stimulation with domoate or test substance is corrected for the mean basal fluorescence (in NN).

Fluorescence of domoate in the presence of test substance is expressed relative to the domoate response alone.

25-75% inhibition of the domoate stimulation must be obtained before calculating the $IC_{50}$.

The test value will be given as $IC_{50}$ (the concentration (μM) of test substance, which inhibits 50% of the domoate induced $Ca_i$ elevation), calculated either from a concentration/response curve or from the formula $$IC_{50} = (\text{applied test substance concentration, μM}) \times \frac{1}{\left(\frac{C_o}{C_x} - 1\right)}$$

where $C_o$ is domoate stimulated $Ca_i$ accumulation in control assays, and $C_x$ is the domoate stimulated $Ca_i$ in the presence of test compound.

The result of this determination is presented in Table 1 below.

TABLE 1

| | Functional Data | |
|---|---|---|
| | GluR5 Activity | GluR6 Activity |
| Compound No. | $IC_{50}$ (μM) | |
| Compound 1a | 1.1 | 32 |
| Compound A1 | 1.5 | 10 |
| Compound E2 | 1.2 | 70 |
| Compound C14 | 1.3 | 37 |

The invention claimed is:

1. An aryl ureido compound, represented by Formula IIa,

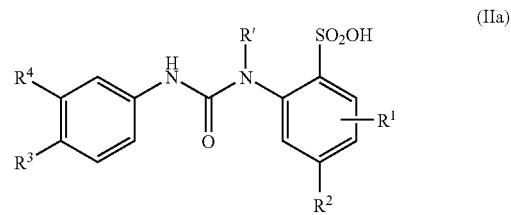

wherein,
- R' represents hydrogen or alkyl; and
- $R^1$ represents hydrogen or alkyl; and
- $R^2$ represents halo; and
- $R^3$ and $R^4$, independently of each another, represent hydrogen, halo, hydroxy, alkoxy, haloalkyl; or
- $R^3$ and $R^4$ together form a methylenedioxy ring of the structure —O—CH$_2$—O—; or
- $R^3$ and $R^4$ together form a benzo-fused ring, which fused ring is optionally substituted one or more times with substituents selected from halo, hydroxy, alkoxy and haloalkyl or an enantiomer or a mixture of enantiomers, or a pharmaceutically acceptable addition salt thereof.

2. The aryl ureido compound of claim 1, which is

2-[3-(3-Bromo-phenyl)-ureido]-4-chloro-5-methyl-benzenesulfonic acid;

4-Chloro-5-methyl-2-[3-(3-trifluoromethyl-phenyl)-ureido]-benzensulphonic acid;

4-Chloro-2-[3-(3-trifluoromethyl-phenyl)-ureido]-benzensulphonic acid;

2-[3-(3-Bromo-phenyl)-ureido]-4-chloro-benzenesulfonic acid; or

4-Chloro-5-methyl-2-(3-naphthalen-2-yl-ureido)-benzensulphonic acid;

or an enantiomer or a mixture of enantiomers, or a pharmaceutically-acceptable addition salt thereof.

3. A pharmaceutical composition comprising a therapeutically effective amount of a chemical compound of claim 1, or a pharmaceutically-acceptable addition salt thereof, and a pharmaceutically acceptable carrier.

* * * * *